United States Patent [19]
Butler

[11] Patent Number: 5,264,675
[45] Date of Patent: * Nov. 23, 1993

[54] METHOD AND APPARATUS FOR DESTROYING A SYRINGE NEEDLE

[76] Inventor: William F. Butler, 680 Atlanta Country Club Dr., Marietta, Ga. 30067

[*] Notice: The portion of the term of this patent subsequent to Feb. 25, 2009 has been disclaimed.

[21] Appl. No.: 840,102

[22] Filed: Feb. 24, 1992

Related U.S. Application Data

[63] Continuation-in-part of Ser. No. 532,021, Jun. 1, 1990, Pat. No. 5,091,621.

[51] Int. Cl.⁵ .......................... B23H 9/00; H05B 3/00
[52] U.S. Cl. ...................................................... 219/68
[58] Field of Search ............................ 219/68; 83/944

[56] References Cited

U.S. PATENT DOCUMENTS

| | | | |
|---|---|---|---|
| 3,770,930 | 11/1973 | Tang | 200/61.64 |
| 4,275,628 | 6/1981 | Greenhouse | 83/167 |
| 4,315,448 | 2/1982 | Ball | 83/167 |
| 4,404,881 | 9/1983 | Hanifl | 83/167 |
| 4,531,437 | 7/1985 | Szablak et al. | 83/165 |
| 4,628,169 | 12/1985 | Ch'ing-Lung | 219/68 |
| 4,877,934 | 10/1989 | Spinello | 219/68 |
| 4,890,006 | 12/1989 | Huang | 200/11 C |
| 4,961,541 | 10/1990 | Hashimoto | 241/65 |
| 5,076,178 | 12/1991 | Kohl et al. | 219/68 |
| 5,091,621 | 2/1992 | Butler | 219/68 |
| 5,138,125 | 8/1992 | Salesses | 219/68 |

FOREIGN PATENT DOCUMENTS 2-52652  2/1990  Japan.

Primary Examiner—Geoffrey S. Evans
Attorney, Agent, or Firm—Jones & Askew

[57] ABSTRACT

A method and apparatus for destroying a syringe needle, having a housing, first and second walls in opposed relationship in the housing and defining therebetween a needle burn chamber, the distance between the first and second surfaces being at least the length of the needle, the first surface defining a first opening therethrough, needle receiver in the chamber movable between the first and second surfaces and defining a second opening therethrough which is coaxial with the first opening, a first electrical contact on the needle receiver, a first electrical contact on the needle receiver, a second electrical contact on the second surface and being in association with the second opening, power source connected to the first and second contacts, a waste collector disposed in the housing beneath and in communication with the burn chamber, the waste collector being removable from the housing, and spring loaded needle guide for moving the needle receiver toward the first opening; so that when the needle is inserted through the first and second openings to be in contacting relationship to the needle receiver and the needle receiver is moved toward the second surface, the tip of the needle engages the second contact closing the circuit between the contacts and melting the needle along at least most of its length with the resultant melted waste falling into the waste collector.

22 Claims, 3 Drawing Sheets

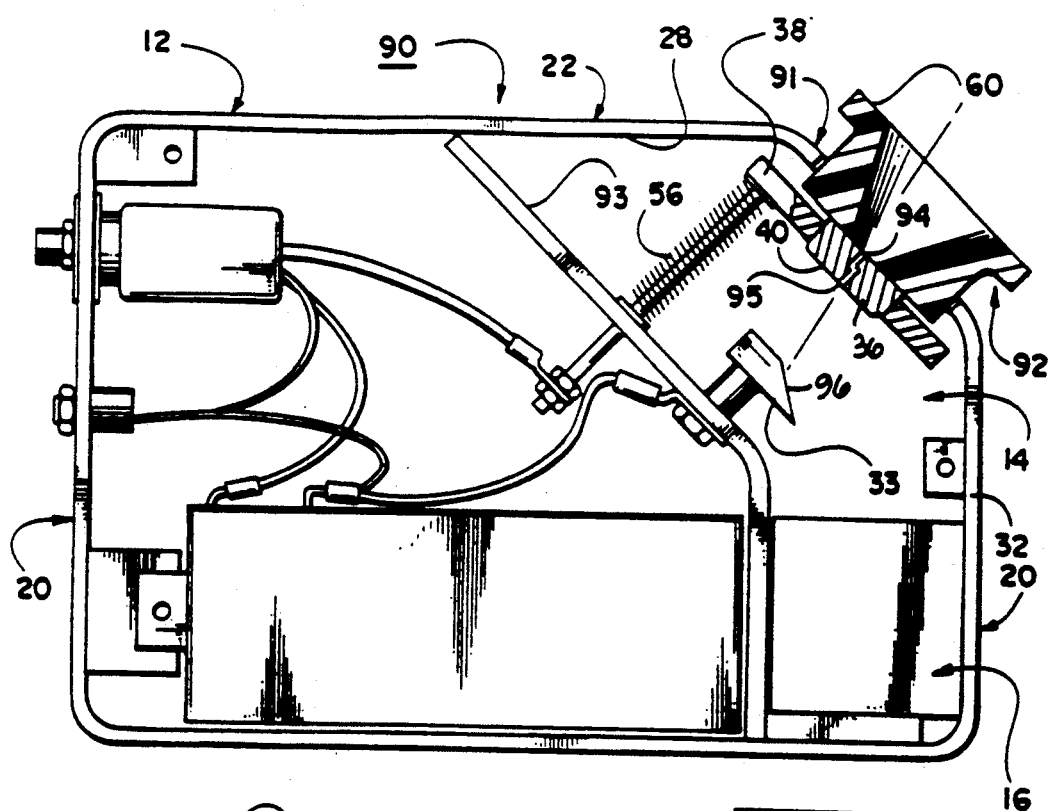
Fig_4
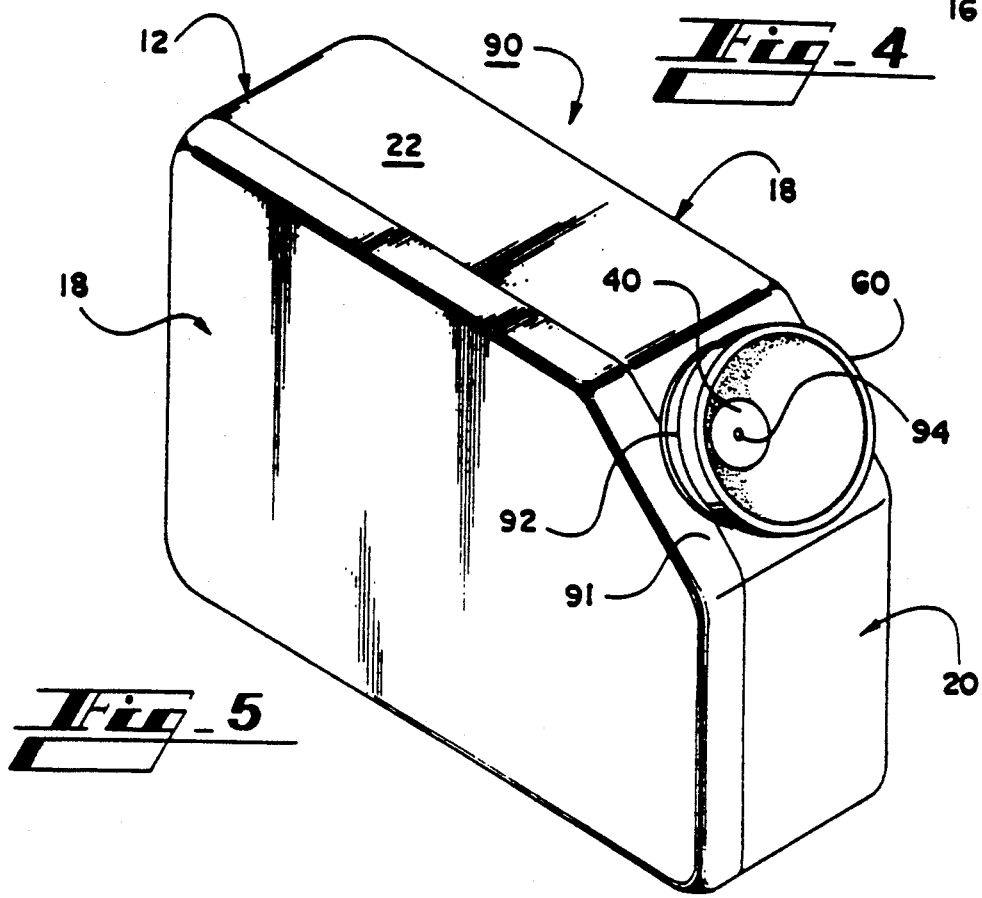
Fig_5

METHOD AND APPARATUS FOR DESTROYING A SYRINGE NEEDLE

CROSS-REFERENCE TO RELATED APPLICATION

This is a continuation-in-part of pending U.S. patent application Ser. No. 07/532,021, filed Jun. 1, 1990, now U.S. Pat. No. 5,091,621.

TECHNICAL FIELD

This invention relates to a method and apparatus for destroying the needle portion of a syringe. In particular, the present invention relates to a method and apparatus that heats, sterilizes and removes the needle portion of a syringe after the syringe has been used on a patient.

BACKGROUND OF THE INVENTION

The threat of infectious diseases, in particular AIDS and hepatitis B, is very prevalent today in hospitals and doctors' offices as a result of the use of hypodermic syringes. The Centers for Disease Control in Atlanta has extensively studied accidental syringe sticking incidents and have logged where most of the accidents occur and to whom. The Centers' records indicate that nurses experience more incidents than most other medical personnel.

Recovering the needle with the plastic tip cover provided with the syringe after use has not solved the problem because the cover can slip off or a person can be stuck by merely attempting to place the cover on the needle. Other means presently utilized for the disposal of used syringes still leave the steel of the hypodermic needle on the syringe, thereby exposing the waste handlers to the possibility of being pricked. The present syringe disposal systems are also very expensive.

The prior art includes the apparatus disclosed in U.S. Pat. No. 4,628,169 which describes an apparatus for melting only the tip of the needle, with the remainder of the metal on the syringe being detached by a separate operation. The remaining metal portion may still be contaminated. That system still leaves the possibility of the person collecting the remaining needle portion being exposed to microorganisms. Also, any infectious fluids are still available to flow out of the now-open plastic portion of the syringe.

U.S. Pat. No. 4,877,934 discloses a needle destroying apparatus which utilizes converging electrodes. The hypodermic syringe is inserted into the apparatus in a vertical orientation and is either slid onto a bottom electrode ramp or an electrode that can slide toward the bottom electrode thereby destroying the needle. However, because of the vertical orientation of the needle as it is inserted into the apparatus, the burnt needle tends to bend away from the ramp and loses contact with the bottom electrode. In addition, because of the vertical orientation, the burnt needle tends to collect on the bottom electrode thereby fouling the surface of the bottom electrode.

What is needed is a needle destruction apparatus that is easy to operate and will reliably destroy the needle efficiently. What is further needed is an apparatus that can be used in the clinic that can be used for long periods of time before it has to be taken apart and cleaned. An apparatus is needed that will treat used syringes to prevent storage of live viruses and other microorganisms in unsealed containers at room temperature, causing unwanted aerosol vapor to contaminate room air breathed by health care workers and patients.

SUMMARY OF THE INVENTION

The above disadvantages of the prior art are overcome by the present invention which comprises a device that electrically heats and destroys the entire steel needle portion of the hypodermic syringe. While applying a safe, low voltage to the steel portion of the needle, the steel melts below the plastic portion of the syringe, welding closed the hollow portion of the needle to prevent any fluid in the syringe to flow from it. The apparatus is designed so that the needle is inserted into the apparatus in a non-vertical orientation. The sterilized melted metal is collected for easy removal and can be discarded in an ordinary trash container.

The present invention is an apparatus for destroying a syringe needle comprising a housing and first and second non-horizontally oriented walls in opposed relationship in the housing and defining therebetween a needle burn chamber. The distance between the first and second surfaces is at least the length of the needle and the first surface defining a first opening therethrough. The apparatus further comprises a non-vertically oriented needle receiving means with a guide means comprising posts between the surfaces and a biasing means comprising springs on the posts in the chamber movable between the first and second surfaces and defining a second opening therethrough which is coaxial with the first opening, a first electrical contact on the needle receiving means, a second electrical contact on the second surface, and being in registry with the second opening. A power means is connected to the first and second contacts with a means for normally biasing the needle receiving means toward the first opening so that when the needle is inserted in a non-vertical manner through the first and second openings to be in contacting relationship to the needle receiving means and the needle receiving means is moved toward the second surface, the tip of the needle engages the second contact closing the circuit between the contacts and melting the needle along at least most of its length.

The device further comprises a housing having a battery power source, such as a 12-volt battery, and associated circuitry. A needle burning chamber is provided in the housing that has a stationary first electrical contact that is mounted on one wall of the chamber. The second contact is mounted on a needle receiving means that is movable within the chamber from a first position adjacent an opening in another wall of the chamber to a second position adjacent the other wall and the first contact. The needle receiving means is normally spring-biased in the first position. Optionally, a waste receiving means is located beneath the burning chamber. The battery can be readily or continuously re-charged. In addition, the apparatus can be operated from conventional 110 volt or 220 volt power sources.

The needle receiving means comprises a metal ring to which the second contact is connected. An opening is provided in the center of the ring that is in registry with the opening in the burning chamber wall.

In operation, the power source is energized and the metal needle portion is inserted in a non-vertical manner into the needle receiving means which is then pushed toward the back wall of the burning chamber and the first electrical contact. When the tip of the needle engages that contact, the needle completes the circuit and acts as a jumper between the two electrical contacts. The current then begins to melt the needle along its length as the needle receiving means is continually pushed towards the first contact. The melted metal drops into an optional waste receiving means to be collected at a later time.

The plastic portion of the needle is then withdrawn from the needle receiving means. It can be retrieved for recycling or can disposed of by conventional waste handling methods.

It is, therefore, an object of the present invention to provide a safe, low cost, efficient and easy to use device for the destruction of the metal needle of a hypodermic syringe, thereby killing any infectious microorganism that may be present in or on the needle.

Another object of the present invention is to completely remove the metal needle from a syringe while simultaneously sealing the plastic portion of the syringe.

Another object of the present invention is to provide an apparatus that can be used for long periods of time between cleaning of electrodes.

Another object of the present invention is to provide an apparatus that will reliably sterilize hypodermic needles.

Yet another object of the present invention is to provide an apparatus that can reliably and safely sterilize and destroy the needle portion of a hypodermic syringe and can be used safely in a clinic or in a physician's office.

Another object of the present invention is to provide an apparatus that can sterilize and destroy the needle portion of a hypodermic syringe so that the destroyed residue of the needle portion can be safely and inexpensively disposed of by conventional means.

These and other objects, features and advantages of the present invention will become apparent after a review of the following detailed description of the disclosed embodiments and the appended claims.

BRIEF DESCRIPTION OF THE DRAWINGS

FIG. 4 is a cross-sectional view of an alternative embodiment.

FIG. 5 is a perspective view of the device of FIG. 4.

DETAILED DESCRIPTION

The present invention is a method and apparatus for destroying the needle portion of a hypodermic syringe. The present invention is, in part, an apparatus that is capable of simultaneously sterilizing and destroying the needle portion of a hypodermic syringe and thereby eliminating the risk of infection by a microorganism that may be present in or on the needle.

When a syringe is inserted into the apparatus that comprises the present invention, the needle is heated to a temperature of at least 1750° C. This temperature is capable of inactivating any virus, bacteria, yeast or other microorganism. In addition to being heated, the needle is melted so that it is removed from the remaining portion of the syringe. The nub remaining after the needle is melted is sealed so that no fluid can leak from the syringe.

Figure 1:
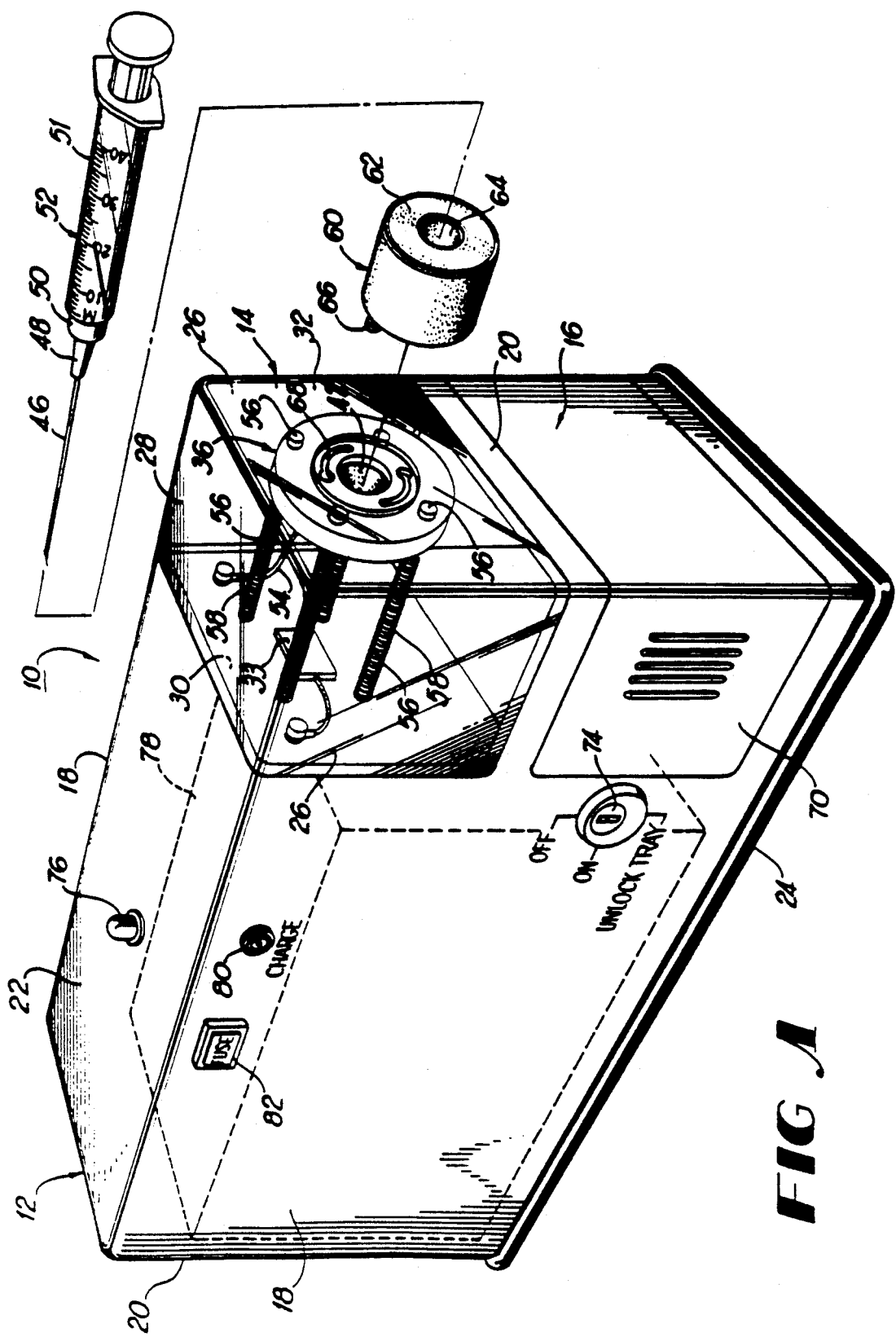
FIG. 1 is a perspective view of the present invention with the needle guide means and a syringe in exploded view away for clarity.

Referring now to FIG. 1, the numeral 10 denotes generally the present invention which comprises a housing 12, a burning chamber 14 and waste collection means 16. The housing 12 can be made of any suitable material, such as metal, plastic or the like, and is generally rectangular in shape with side walls 18, end walls 20 and top 22. A support flange 24 extends about the bottom periphery of the housing 12 to provide stability for the device when it is placed on a suitable support surface. It is to be understood that the apparatus according to the present invention can be mounted to a wall or a surface such as the bottom of a wall cabinet.

The burning chamber 14 occupies the upper quadrant of one end of the housing 12 and preferably is constructed of a heat resistant material. The chamber 14 is defined by side walls 26, a top 28, rear wall 30 and front wall 32. A first electrical contact 33 is mounted on rear wall 30 in registry with an opening 34 centrally disposed through front wall 32.

Figure 2:
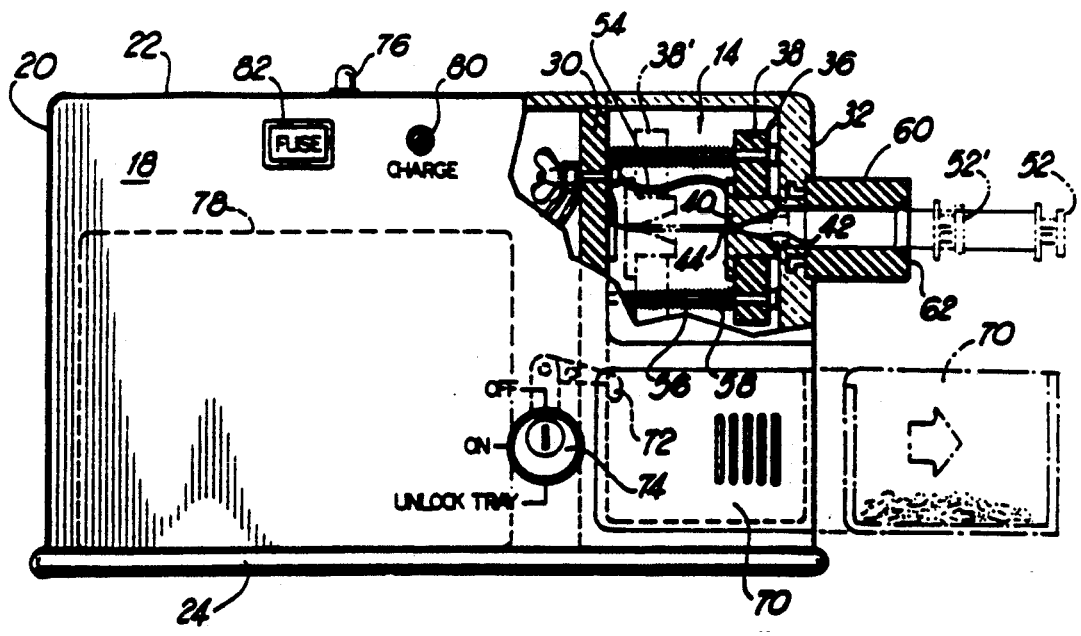
FIG. 2 is a side elevational view in partial cross-section of the invention.

As seen more clearly in FIG. 2, a needle receiving means 36 is provided within the chamber 14 and comprises a circular, non-conductive plate 38 having a electrically conductive plug 40 positioned through its center. A conical shaped port 42 is disposed through the front face of the plug 40 adjacent wall 32 and which tapers downwardly through the interior of the plug 40 to terminate in opening 44 which exits the rear face of plug 40. The port 42 and opening 44 are dimensional to receive the metal needle portion 46, the neck portion 48 and shoulder portion 50 on body portion 51 of the hypodermic needle 52. Wire 54 connects the plug 40 with the electrical circuitry within housing 12 through rear wall 30.

The plate 38 is mounted within the chamber 14 for movement between a rest position adjacent opening 34 and an operative position as shown in phantom lines in FIG. 2 at 38' adjacent the rear wall 30 along a plurality of posts 56 that extend outwardly from wall 30. The plate 38 is normally biased in its rest position by springs 58.

Needle guide means 60 is provided on the wall 32 exteriorly of the chamber 14 and comprises a circular element 62 having a central bore 64 therethrough. The element 62 is detachably mounted to the wall 32 by means of bayonet lugs 66 which are engageable within complementary slots 68 on wall 32. The size of bore 64 depends on the diameter of the needle body 51 utilized. Thus, a different sized needle 52 would require its own respective guide means 60 to be placed on the wall 32.

The diameter of opening 44 can be of such size as to accept conventional 22-, 18-, 14- or any other gauge stainless steel needles therethrough. Additionally, the device 10 may incorporate a plurality of needle receiving means so that a single device 10 may be used to destroy a number of different style and diameter needles, such as, for example, intravenous, butterfly and catheter placement needles.

The optional waste collection means 16 is disposed beneath and in communication with the burn chamber 14 and comprises a tray 70 that is slidably removable from housing 12, as shown in FIG. 2. The tray 70 receives therein the melted needles that result from the operation of the device 10.

The tray 70 is retained within the housing 12 by means of a locking arm 72 that is operatively connected to the keylock switch 74. The switch 74 is a safety feature, ensuring that only authorized personnel operate the device 10. The "unlock tray" position of the switch 74 releases the locking arm 72 and allows the tray 70 to be removed.

A LED light 76 is positioned on top 22 that is on when the switch 74 is moved to the "ON" position. The power source is normally a 12-volt battery 78 that is rechargeable through charging opening 80 in side wall 18. The fuses 82 within the housing 12 are reached through fuse opening 83. A second LED light, not shown, may be provided to indicate that the charging circuit is in use. A conventional breaker can be used in place of the fuse.

OPERATION

To operate the device 10, a key is inserted into switch 74 which is turned to the "ON" position, which in turn allows electricity to flow from battery 78 to contact 33 and to plug 40. The light 76 will also be illuminated, indicating that the device 10 is operative.

The user inserts the needle 52 into bore 64 until the shoulder 50 engages the port 42. The needle portion 46 then receives current along its length through plug 40. The position of the needle 52 at that time is shown in FIG. 2 at numeral 52'. The distance between the contact 33 and plug 40 is at least equal to the length of the needle portion 46 desired to be melted.

The user begins to push the needle 52 through the element 62, thereby moving plate 38 towards wall 30 until the tip of the needle portion 46 engages contact 33. The needle portion 46 then acts as a jumper between contact 33 and plug 40, closing the circuit and melting the needle portion 46. Continued pushing of the needle 52 causes the plate 38 to assume its position 38', at which time, the majority of the metal needle portion 46 has melted off of the needle 52 and has fallen into the tray 70.

The user then withdraws the needle 52 from the device 10, allowing the plate 38 to assume its rest position. At that time, another needle 52 may be inserted into the device 10 or the device 10 can be de-energized by turning the switch 74 to the "OFF" position. The light 76 will then go off, indicating that the device 10 is inoperative.

When enough waste has been collected in tray 70, it can be removed by turning the switch 74 to the "UNLOCK TRAY" position. The contents of the tray 70 are sterile, so they can be disposed of as normal waste materials. The tray 70 will contain no sharp metal so incidents of sticking will be eliminated. The remaining body portion 51 of the needle 52 can be recycled as sterilized plastic.

ALTERNATIVE EMBODIMENT

Figure 3:
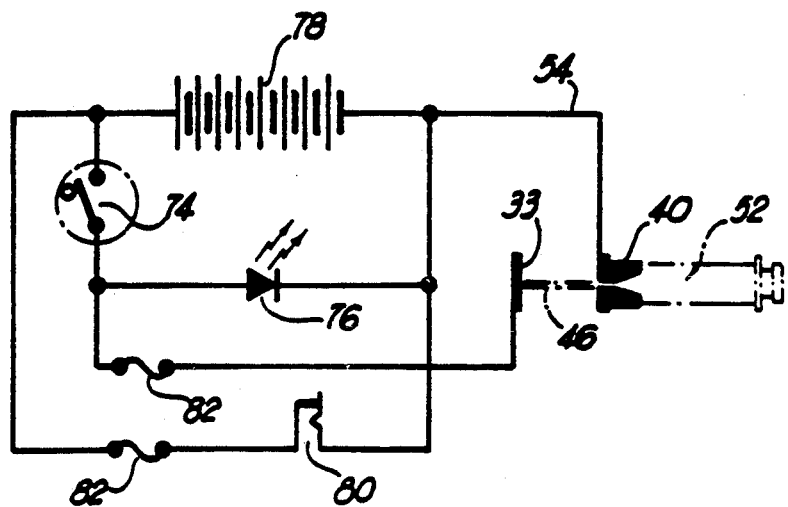
FIG. 3 is a schematic of the electrical circuitry of the present invention.

An alternative embodiment 90 is shown in FIGS. 4 and 5. The alternative embodiment is similar in structure to the invention shown in FIGS. 1–3 and described above except that the needle guide means 60 is angled with respect to the housing top 22. The alternative embodiment includes the top 22, side walls 18 and end walls 20 as in the embodiment described above. In addition, the alternative embodiment 90 includes an angled face 91 which slidably receives the needle guide means 60. The needle guide means 60 of the alternative embodiment 90 includes a shoulder 92 which rests against the angled face 91 during operation.

The alternative embodiment 90 includes a burning chamber defined by side walls 26, the top 28, the face 91 and an angled rear wall 93. The first electrical contact 33 is mounted on the angled rear wall 93. In the alternative embodiment, the contact 33 has a sloped face 96. The needle receiving means 36 is coaxial with and secured to the needle guide means 60. The needle receiving means 36 includes the conductive plate 38 having the plug 40 positioned through its center. The plug 40 has an opening therethrough. The opening comprises a first length 94 and a second parallel length 95. The axis of the first length 94 is non-coaxial with the axis of the second length 95 as shown in FIG. 4. The non-coaxial orientation of the first length 94 and the second length 95 ensures that there will be good contact between the needle 46 and the needle receiving means 36. In addition, the non-coaxial orientation prevents sparks from escaping from the interior of the burning chamber 14.

The plate 38 is mounted for slidable movement relative to the angled rear wall 93 along the posts 56.

It is to be understood that an important part of the present invention is that the needle must be inserted in a non-vertical orientation. The angle from the vertical can be between 10° and 90° with the more preferred angle range of between 20° and 75° with the most preferred angle range of approximately 45°.

In the operation, the alternative embodiment functions similarly to the invention 10. The user inserts the needle 52 into the needle guide means 60 and into the first length 94 of the plug 40. The needle 52 is then fed through the second length of the plug 40 until it contacts the angled face 96 of the electrical contact 33. The electrical circuit is closed when the tip of the needle 52 contacts the sloped face 96 and the plug 40. The off-set axes of the first and second plug lengths 94, 95 help to maintain electrical contact during the entire operation. Once electrical contact is established, the user continues to press against the needle guide means until a majority of the needle portion 46 has melted off the needle 52 and has fallen into the tray 70.

It will be appreciated that the embodiments discussed above are the preferred embodiments, falling within the scope of the appended claims, and that various other alternative embodiments are contemplated. For example, the angle of the face 91 in the alternative embodiment 90 may be altered to accommodate the user. Moreover, it is contemplated that the off-set axes of the first and second lengths of the plug may be incorporated into the first embodiment.

What is claimed is:

1. An apparatus for destroying a syringe needle comprising:
    a) a housing;
    b) first and second non-horizontally oriented surfaces in opposed relationship in a housing and defining therebetween a needle burn chamber, the distance between the first and second surfaces being at least the length of the needle, the first surface defining a first opening therethrough;
    c) a non-vertically oriented needle receiving means with guide means comprising posts between the surfaces and a biasing means comprising springs on the posts in the chamber movable between the first and second surfaces and defining a second opening therethrough which is coaxial with the first opening;
    d) a first electrical contact on the needle receiving means;
    e) a second electrical contact on the second surface and being in association with the second opening;
    f) power means connected to the first and second contacts;

g) means for normally biasing the needle receiving means toward the first opening; so that when the needle is inserted in a non-vertical manner through the first and second openings to be in contacting relationship to the needle receiving means and the needle receiving means is moved toward the second surface, the tip of the needle engages the second contact closing the circuit between the contacts and melting the needle along at least most of its length.

2. The apparatus of claim 1, further comprising guide means between the first and second surfaces, the needle receiving means being movable therealong and the biasing means on the guide means.

3. The apparatus of claim 2, wherein the needle receiving means is a circular plate.

4. The apparatus of claim 2, wherein the guide means is angled with respect to the first and second walls.

5. The apparatus of claim 2, wherein the guide means and the needle receiving means are parallel.

6. The apparatus of claim 1, and further comprising a needle guide means detachably mounted on the needle receiving means exteriorly of the housing, the guide means having a channel therethrough of a specific diameter corresponding to the diameter of the needle.

7. The apparatus of claim 1, further comprising a waste collecting means disposed in the housing beneath and in communication with the burn chamber.

8. The apparatus of claim 1, wherein the first and second surfaces are oriented at between approximately 10° and 90° from the vertical.

9. The apparatus of claim 1, wherein the first and second surfaces are oriented at between approximately 20° and 75° from the vertical.

10. The apparatus of claim 1, wherein the needle receiving means is oriented approximately 45° from the vertical.

11. The apparatus of claim 1, wherein the axes of the first and second openings are parallel and non-coaxial.

12. The apparatus of claim 1, wherein the needle receiving means has an exterior surface and an interior surface, and the second opening through the needle receiving means is defined by a first axial length extending from the exterior surface, and a second axial length in communication with the first axial length and extending from the interior surface, the first and second axial lengths being non-coaxial.

13. The apparatus of claim 12, wherein the first and second axial lengths are parallel.

14. A method of destroying a syringe needle, having a metal portion, comprising the steps of:
 a) inserting the metal portion of a needle through a non-vertically oriented needle receiving means with guide means comprising posts and a biasing means comprising springs on the posts into a needle burn chamber having a first electrical contact on the needle receiving means and a second electrical contact on a wall of the chamber opposite the needle receiving means;
 b) energizing the contacts;
 c) moving the needle receiving means toward the wall until the metal portion engages the second electrical contact, closing the circuit between the contacts; and
 d) pushing continuously the needle receiving means toward the wall until at least a major portion of the metal portion is melted along its length.

15. The method of claim 14, wherein the guide means is angled with respect to the first and second walls.

16. The method of claim 14, wherein the guide means and the needle receiving means are parallel.

17. The method of claim 14, wherein the axes of the first and second openings are parallel and non-coaxial.

18. The method of claim 14, wherein the non-vertically oriented needle receiving means is between approximately 10° and 90° from the vertical.

19. The method of claim 14, wherein the non-vertically oriented needle receiving means is between approximately 20° and 75° from the vertical.

20. The method of claim 14, wherein the non-vertically oriented needle receiving means is approximately 45° from the vertical.

21. The method of claim 14, wherein the needle receiving means has an exterior surface and an interior surface, and the second opening through the needle receiving means is defined by a first axial length extending from the exterior surface, and a second axial length in communication with the first axial length and extending from the interior surface, the first and second axial lengths being non-coaxial.

22. The method of claim 21, wherein the first and second axial lengths are parallel.

* * * * *